United States Patent
Okamoto

(10) Patent No.: US 10,736,493 B2
(45) Date of Patent: Aug. 11, 2020

(54) INSERTING DEVICE

(71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 241 days.

(21) Appl. No.: 15/016,749

(22) Filed: Feb. 5, 2016

(65) Prior Publication Data

US 2016/0150945 A1    Jun. 2, 2016

Related U.S. Application Data

(63) Continuation of application No. PCT/JP2014/063486, filed on May 21, 2014.

(30) Foreign Application Priority Data

Aug. 6, 2013    (JP) ................................. 2013-163202

(51) Int. Cl.
     *A61B 1/00*      (2006.01)
     *A61B 1/005*      (2006.01)
     (Continued)

(52) U.S. Cl.
     CPC .......... *A61B 1/0016* (2013.01); *A61B 1/0008* (2013.01); *A61B 1/0052* (2013.01);
     (Continued)

(58) Field of Classification Search
     USPC ........ 600/104, 106, 107, 114–116, 121–125, 600/137, 139–152; 604/95.01–95.05,
     (Continued)

(56) References Cited

U.S. PATENT DOCUMENTS 4,928,699 A    5/1990    Sasai
5,348,017 A    9/1994    Thornton et al.
(Continued)

FOREIGN PATENT DOCUMENTS

EP    2 967 636 A1    1/2016
JP    H05-329097 A    12/1993
(Continued)

OTHER PUBLICATIONS

International Search Report dated Aug. 26, 2014 issued in PCT/JP2014/063486.
(Continued)

*Primary Examiner* — Ryan N Henderson
(74) *Attorney, Agent, or Firm* — Scully, Scott, Murphy & Presser, P.C.

(57) ABSTRACT

An insertion device includes a shape-variable tube elastically returning while the shape-variable tube bends at a tube bending radius of a tube radius boundary value or more, and a shaft rotating around a shaft axis inside the shape-variable tube so that the shaft transmits a driving force to drive a motion section from a first extending direction toward a second extending direction. The shaft elastically returns while the shaft bends at a shaft bending radius of a shaft radius boundary value or more, and rotates without being deformed while the elastic return is impossible when the shape-variable tube bends in an elastically returnable range.

7 Claims, 13 Drawing Sheets

(51) Int. Cl.
*A61B 1/31* (2006.01)
*A61B 1/273* (2006.01)

(52) U.S. Cl.
CPC ...... *A61B 1/00078* (2013.01); *A61B 1/00101* (2013.01); *A61B 1/00131* (2013.01); *A61B 1/00133* (2013.01); *A61B 1/00135* (2013.01); *A61B 1/00154* (2013.01); *A61B 1/00156* (2013.01); *A61B 1/2736* (2013.01); *A61B 1/31* (2013.01); *A61B 1/0057* (2013.01)

(58) Field of Classification Search
USPC .................................................. 604/264, 271
See application file for complete search history.

(56) References Cited

U.S. PATENT DOCUMENTS

| | | | |
|---|---|---|---|
| 5,377,682 A | 1/1995 | Ueno et al. | |
| 2004/0243108 A1* | 12/2004 | Suzuki | A61B 17/00234 606/1 |
| 2005/0004432 A1* | 1/2005 | Suzuki | A61B 17/29 600/146 |
| 2006/0270901 A1* | 11/2006 | Bern | A61B 1/0016 600/114 |
| 2008/0033245 A1* | 2/2008 | Kura | A61B 1/00071 600/114 |
| 2009/0171152 A1* | 7/2009 | Aoki | A61B 1/00147 600/114 |
| 2011/0319713 A1 | 12/2011 | Frassica et al. | |
| 2012/0004504 A1* | 1/2012 | Frassica | A61M 25/0017 600/115 |
| 2012/0029281 A1* | 2/2012 | Frassica | A61B 1/00082 600/114 |
| 2013/0035552 A1* | 2/2013 | Moriyama | A61B 1/0016 600/149 |
| 2013/0070255 A1 | 3/2013 | Nagai | |
| 2014/0277005 A1 | 9/2014 | Guggenheimer | |

FOREIGN PATENT DOCUMENTS

| | | | | |
|---|---|---|---|---|
| JP | H06-105797 A | | 4/1994 | |
| JP | 07289549 A | * | 11/1995 | ......... A61B 1/00133 |
| JP | H07-289549 A | | 11/1995 | |
| JP | H11-267090 A | | 10/1999 | |
| JP | 2005253892 A | * | 9/2005 | ........... A61B 1/0016 |
| JP | 2005288035 A | * | 10/2005 | ........... A61B 1/0016 |
| JP | 2013-525076 A | | 6/2013 | |
| WO | 2009/073409 A1 | | 6/2009 | |
| WO | WO 2011/062087 A1 | | 5/2011 | |

OTHER PUBLICATIONS

English translation of International Preliminary Report on Patentability dated Feb. 18, 2016 together with the Written Opinion received in related International Application No. PCT/JP2014/063486.

Extended Supplementary European Search Report dated Mar. 1, 2017 in European Patent Application No. 14 83 4306.4.

* cited by examiner

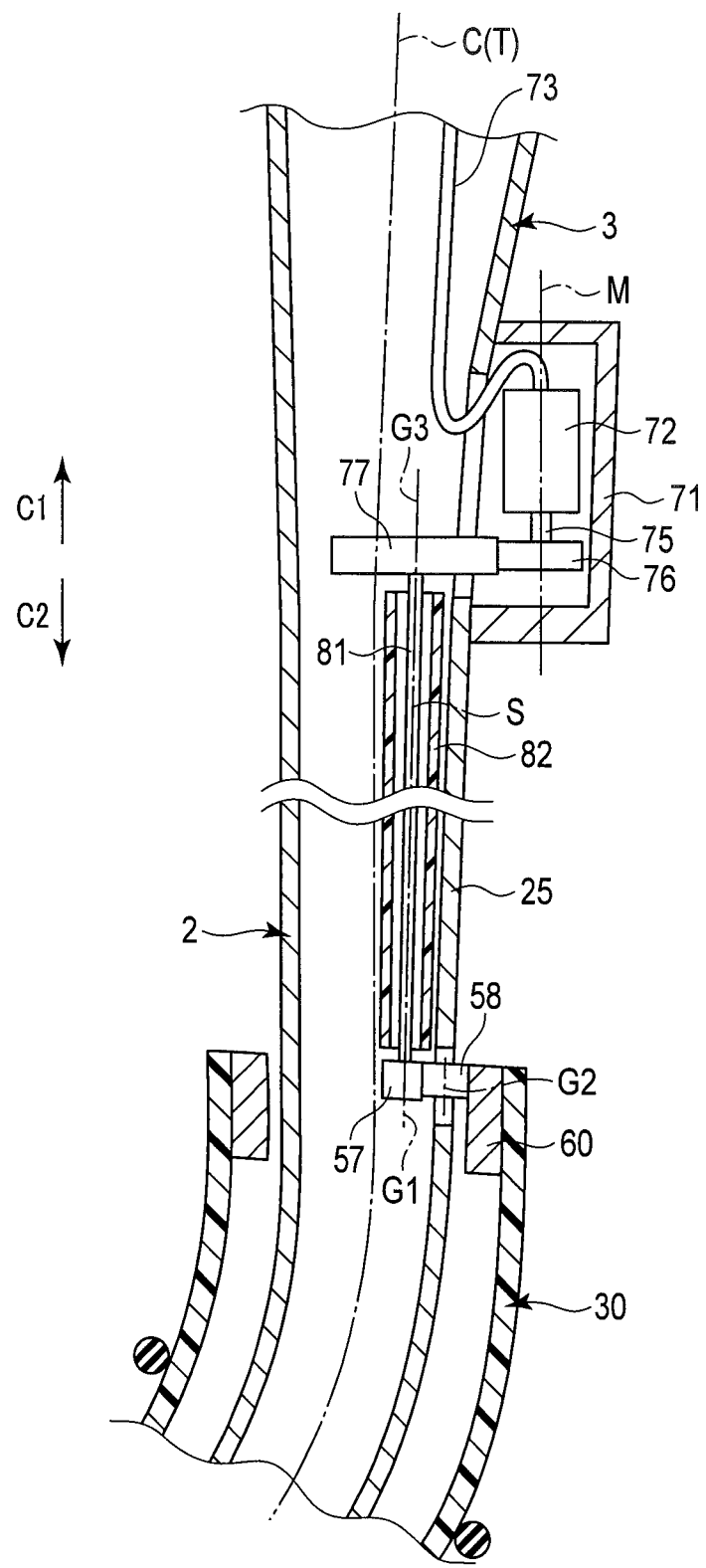
F I G. 2

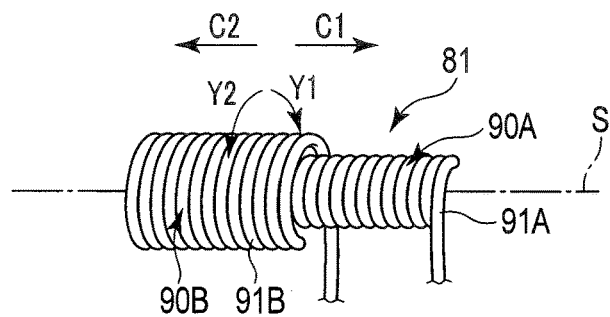
F I G. 6
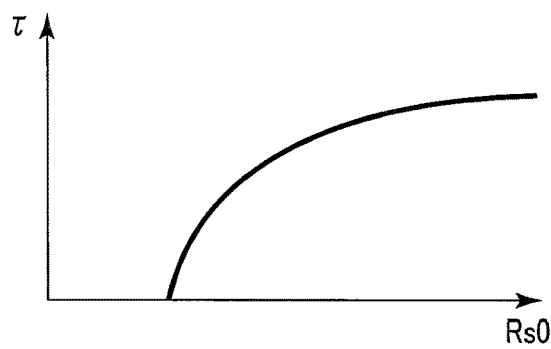
F I G. 7
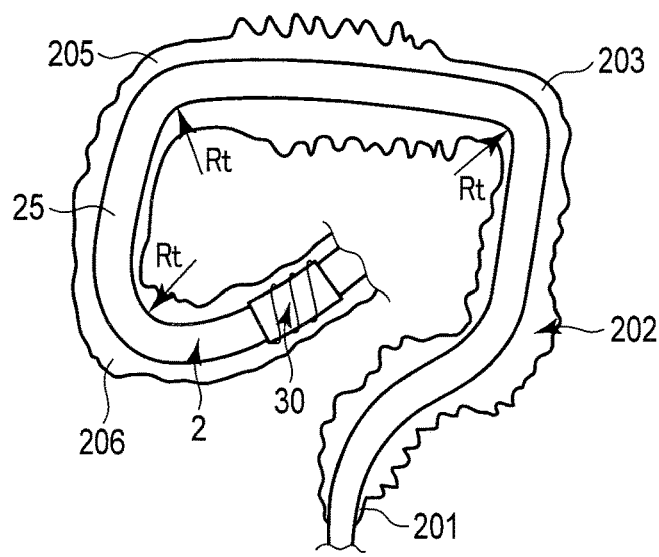
F I G. 8

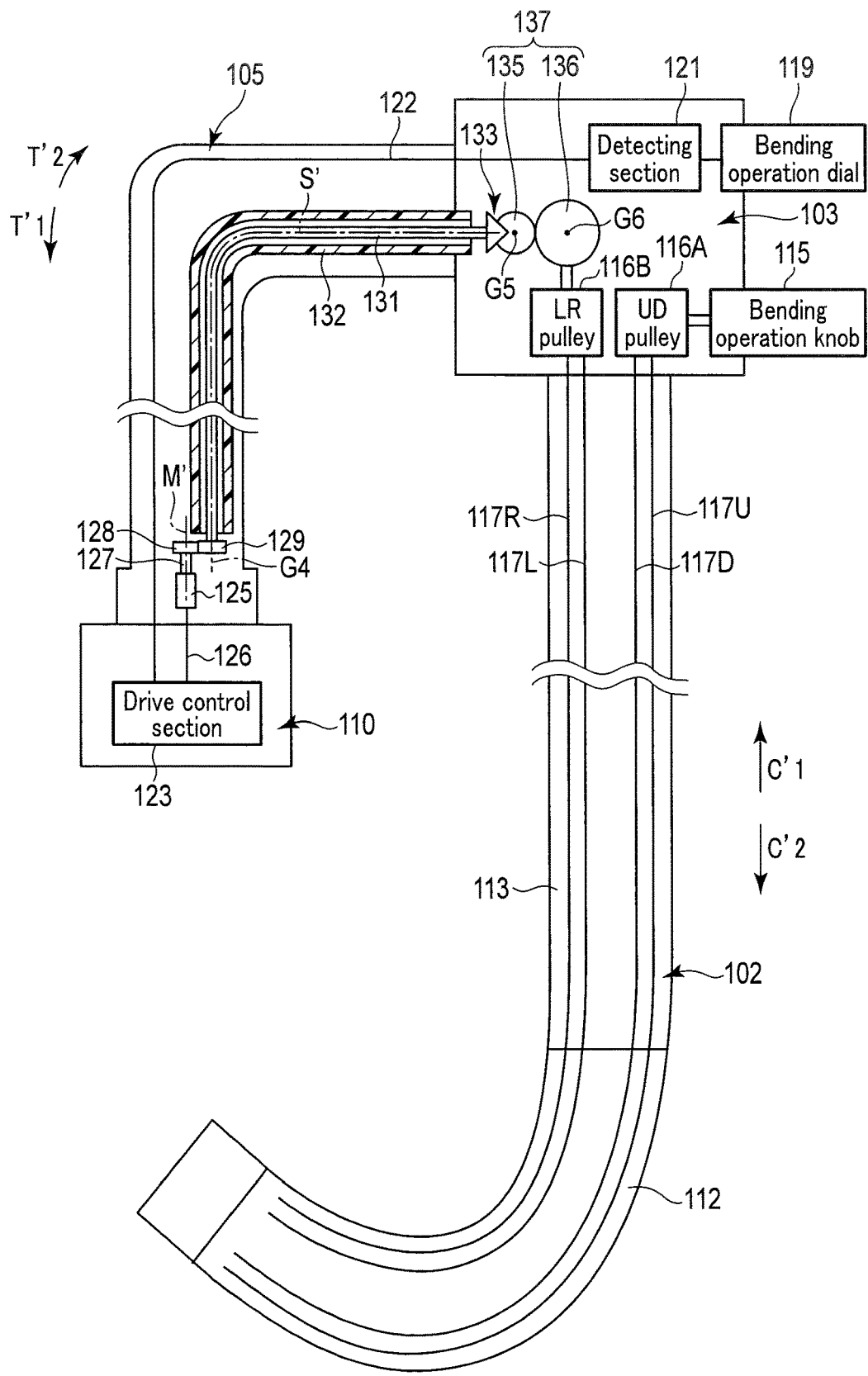
F I G. 13

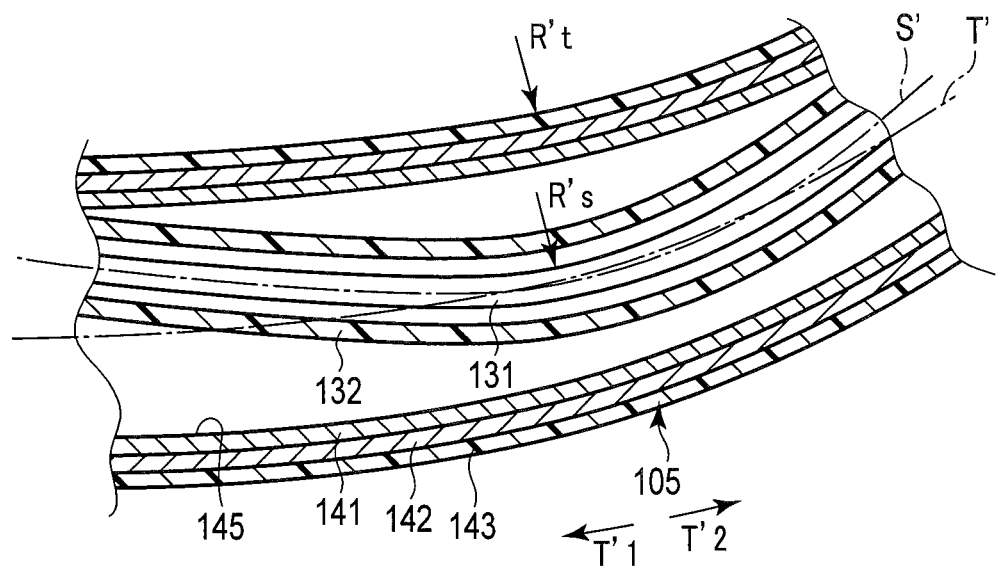
F I G. 14
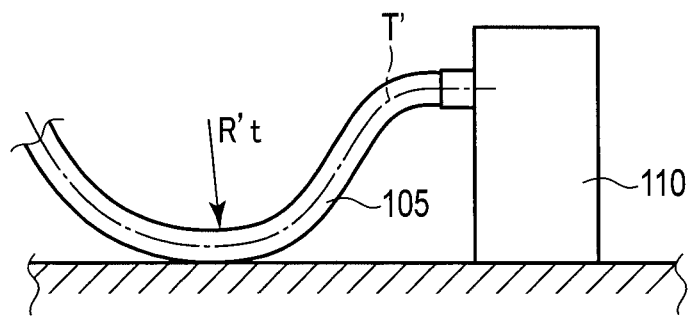
F I G. 15

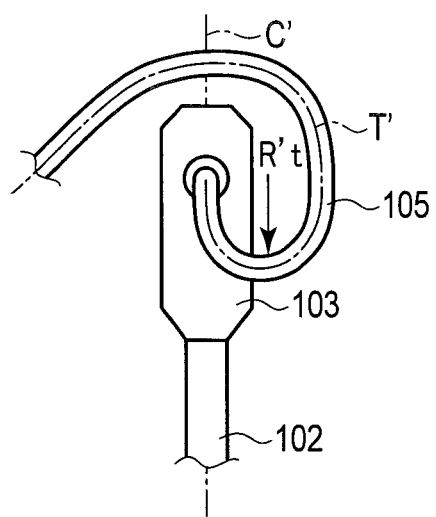
F I G. 16

INSERTING DEVICE

CROSS-REFERENCE TO RELATED APPLICATIONS

This is a Continuation application of PCT Application No. PCT/JP2014/063486, filed May 21, 2014 and based upon and claiming the benefit of priority from prior Japanese Patent Application No. 2013-163202, filed Aug. 6, 2013, the entire contents of which are incorporated herein by reference.

BACKGROUND OF THE INVENTION

1. Field of Invention

The present invention relates to an inserting device including a shaft that rotates around a shaft axis, thereby transmitting a driving force to drive a motion section provided in an inserting section or attached to the inserting section.

2. Description of Related Art

In Jpn. Pat. Appln. KOKAI Publication No. H07-289549, there is disclosed an ultrasonic diagnosis device that is an inserting device in which an ultrasonic transducer that is a motion section is provided in a distal portion of an inserting section extended along a longitudinal axis. In this ultrasonic diagnosis device, a shaft is extended through an inside of a flexible universal cord. The shaft passes through an inside of the operating section, and is extended inside a soft portion (a flexible tube section) having a flexibility in the inserting section from a proximal direction toward a distal direction. A rotational torque acts on the shaft, and hence the shaft rotates around a shaft axis. When the shaft rotates, a driving force to drive the ultrasonic transducer is transmitted to the ultrasonic transducer via the shaft. When the driving force is transmitted, the ultrasonic transducer rotates. In the ultrasonic diagnosis device, diagnosis is performed in a state where the ultrasonic transducer is rotated.

BRIEF SUMMARY OF THE INVENTION

According to one aspect of the invention, an insertion device includes that: an inserting section which is extended along a longitudinal axis; a motion section which is provided in the inserting section or attached to the inserting section, and which is configured to be driven when a driving force is transmitted thereto; a shape-variable tube which has a tube axis extended from a first extending direction toward a second extending direction that is a direction opposite to the first extending direction, and which has a flexibility, the shape-variable tube being configured to elastically return in a case where the shape-variable tube bends at a tube bending radius of a tube radius boundary value or more; and a shaft which has a shaft axis extended inside the shape-variable tube from the first extending direction toward the second extending direction, the shaft being configured to rotate around the shaft axis by an action of a rotational torque so that the shaft transmits the driving force to drive the motion section from the first extending direction toward the second extending direction, the shaft being configured to elastically return in a case where the shaft bends at a shaft bending radius of a shaft radius boundary value or more, the shaft being configured to rotate without being deformed in a state where the elastic return is impossible when the shape-variable tube bends in an elastically returnable range, wherein the shape-variable tube includes a tube inner peripheral surface which is configured to exert a pressing force on the shaft toward the tube axis so that the tube inner peripheral surface maintains the shaft bending radius of the shaft at a size of the shaft radius boundary value or more, in a state where the shaft that is spirally extended rotates by the action of the rotational torque on the shaft.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a cross-sectional view schematically showing a constitution to transmit a driving force to a spiral unit according to the first embodiment;

FIG. 6 is a perspective view schematically showing a constitution of a shaft according to the first embodiment;

FIG. 7 is a schematic view showing a relation between a rotational torque that acts on the shaft according to the first embodiment and a shaft radius boundary value of a shaft bending radius;

FIG. 8 is a schematic view showing a state where the inserting section to which the spiral unit according to the first embodiment is attached is inserted from an anus into a large intestine;

FIG. 13 is a schematic view showing a constitution to transmit a driving force to a bending section according to the second embodiment;

FIG. 14 is a cross-sectional view schematically showing a constitution of a universal cord according to the second embodiment;

FIG. 15 is a schematic view showing an extended state of the universal cord from a peripheral unit when the endoscope device according to the second embodiment is used;

FIG. 16 is a schematic view showing the extended state of the universal cord from an operating section in a certain use state of the endoscope device according to the second embodiment;

DETAILED DESCRIPTION OF THE INVENTION

First Embodiment

Figure 1:
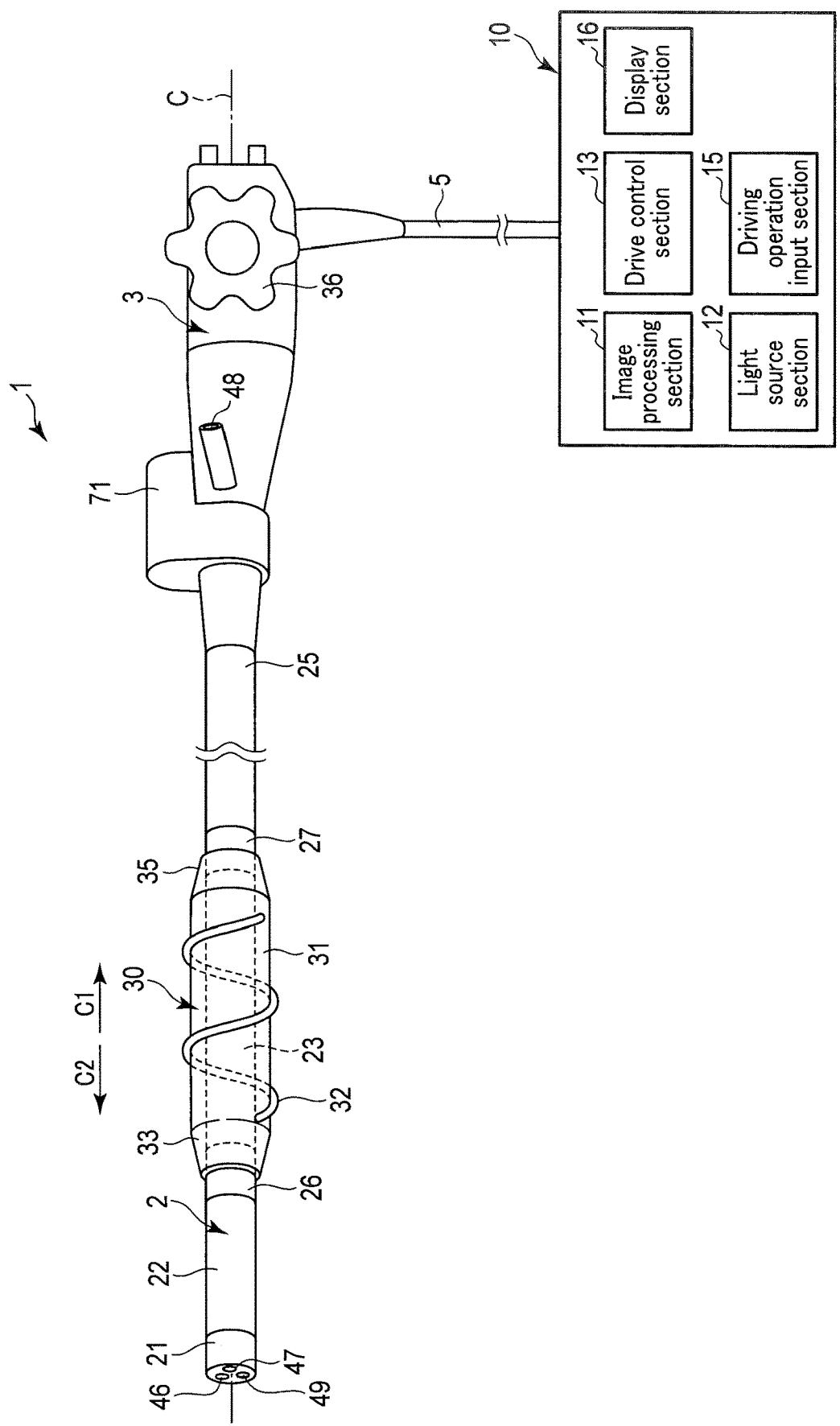
FIG. 1 is a schematic view showing an endoscope device according to a first embodiment of the present invention.

A first embodiment of the present invention will be described with reference to FIG. 1 to FIG. 11. FIG. 1 is a view showing an endoscope device 1 that is an inserting device according to the first embodiment. As shown in FIG. 1, the endoscope device 1 has a longitudinal axis C. One side of directions parallel to the longitudinal axis C (a direction of an arrow C1 of FIG. 1) is a proximal direction, and a direction opposite to the proximal direction (a direction of an arrow C2 of FIG. 1) is a distal direction. Further, the distal direction and the proximal direction become longitudinal axis directions parallel to the longitudinal axis C. The endoscope apparatus 1 includes an inserting section (an endoscope inserting section) 2 extended along the longitudinal axis C, and an operating section (an endoscope operating section) 3 provided on a proximal direction side with respect to the inserting section 2. The inserting section 2 is extended along the longitudinal axis C, and inserted into a body cavity when the endoscope device 1 is used.

One end of a universal cord 5 is connected to the operating section 3. The other end of the universal cord 5 is connected to a peripheral unit 10. The peripheral unit 10 includes an image processing section 11 such as an image processor, a light source section 12 such as a lamp, a drive control section 13, a driving operation input section 15, and a display section 16 such as a monitor. The drive control section 13 is, for example, a control device including a central processing unit (CPU), an application specific integrated circuit (ASIC) and the like, and the driving operation input section 15 is, for example, a foot switch, an operation button or the like.

The inserting section 2 includes a distal rigid section 21 forming a distal end of the inserting section 2, an active bending section 22 disposed on the proximal direction side with respect to the distal rigid section 21, a passive bending section 23 provided on the proximal direction side with respect to the active bending section 22, and a flexible tube section 25 provided on the proximal direction side with respect to the passive bending section 23. The active bending section 22 is connected to the passive bending section 23 by a bending tube connecting portion 26. In addition, the passive bending section 23 is connected to the flexible tube section 25 by a relay connecting portion 27.

On an outer peripheral direction side of the inserting section 2, a cylindrical spiral unit 30 is disposed. The spiral unit 30 is extended along the longitudinal axis C between the bending tube connecting portion 26 and the relay connecting portion 27. In a state where the inserting section 2 is inserted through the spiral unit 30, the spiral unit 30 is attached to the inserting section 2. In a state where the spiral unit 30 is attached to the inserting section 2, a driving force is transmitted, and hence the spiral unit 30 rotates relative to the inserting section 2 in a periaxial direction of the longitudinal axis. That is, the spiral unit 30 is a motion section which is attached to the inserting section 2 and to which the driving force is transmitted to be driven.

The spiral unit 30 includes a base tube 31 extended along the longitudinal axis C. Additionally, on an outer peripheral surface of the base tube 31, a fin portion 32 is disposed. The fin portion 32 is spirally extended from the proximal direction toward the distal direction. On a distal direction side with respect t the base tube 31, a distal side taper portion 33 is provided. The distal side taper portion 33 is formed into a tapered shape so that its outer diameter decreases toward the distal direction side. Additionally, on the proximal direction side with respect to the base tube 31, a cylindrical proximal side taper portion 35 is provided. The proximal side taper portion 35 is formed into a tapered shape so that its outer diameter decreases toward the proximal direction side.

In a state where the fin portion 32 is pressed in an inner peripheral direction by a lumen paries or the like, the spiral unit 30 rotates in one side of the periaxial direction of longitudinal axis, and hence an impulsive force acts on the inserting section 2 in the distal direction. Additionally, in a state where the fin portion 32 is pressed in the inner peripheral direction by the lumen walls or the like, the spiral unit 30 rotates in the other side of the periaxial direction of the longitudinal axis, and hence the impulsive force acts on the inserting section 2 in the proximal direction. Due to the impulsive force toward the distal direction, inserting properties of the inserting section 2 into a lumen improve, and due to the impulsive force toward the proximal direction, pull-out properties of the inserting section 2 from the lumen improve.

Figure 3:
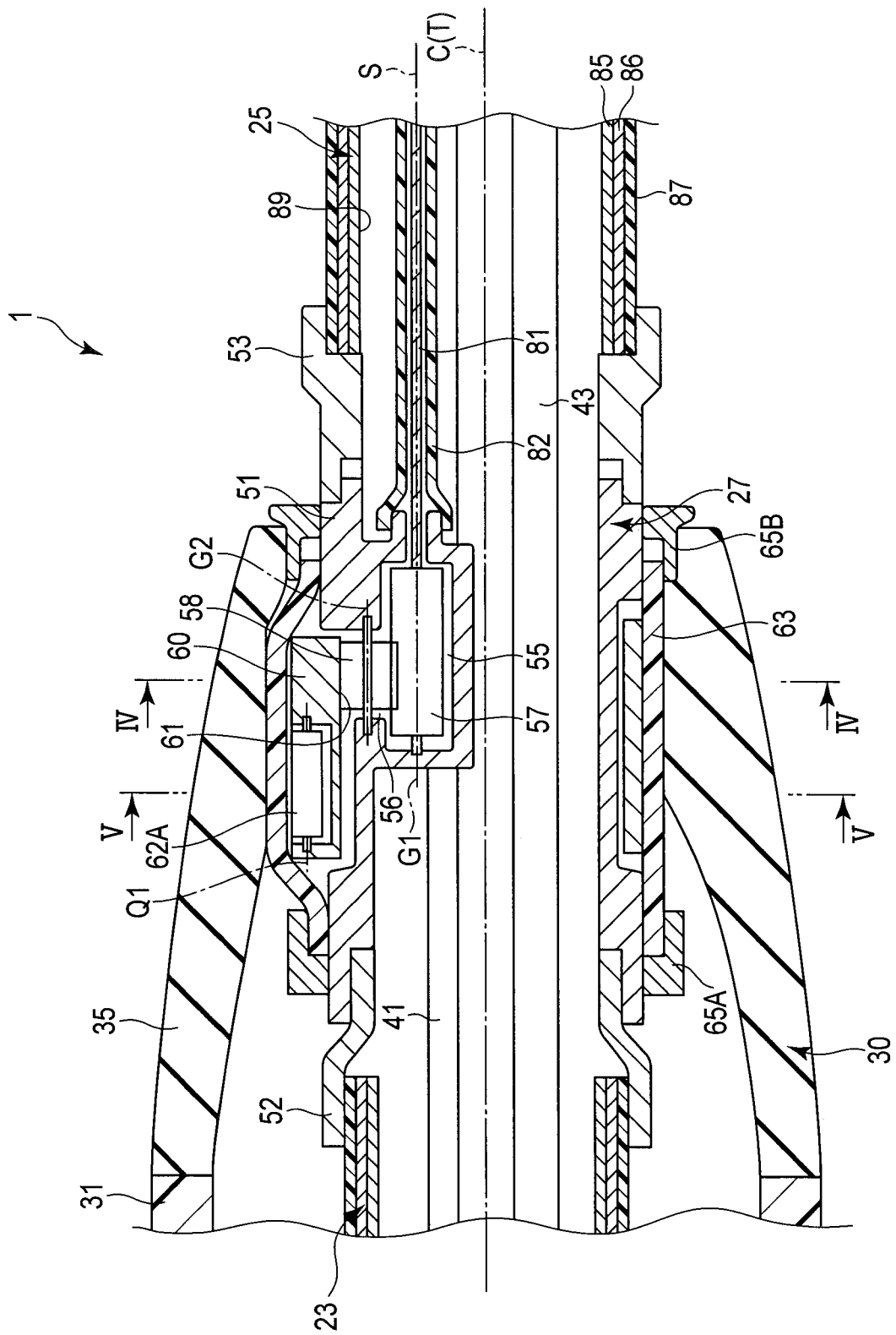
FIG. 3 is a cross-sectional view schematically showing a constitution to attach the spiral unit according to the first embodiment to an inserting section.

FIG. 2 is a view showing a constitution to transmit the driving force to the spiral unit 30. FIG. 3 is a view showing a constitution to attach the spiral unit 30 to the inserting section 2 in the relay connecting portion 27. Additionally, FIG. 4 is a cross-sectional view taken along the IV-IV line of FIG. 3, and FIG. 5 is a cross-sectional view taken along the V-V line of FIG. 3.

As shown in FIG. 1, on an outer surface of the operating section 3, a bending operation knob 36 is disposed in which a bending operation of the active bending section 22 is input. As shown in FIG. 4 and FIG. 5, bending wires 37A and 37B are extended along the longitudinal axis C inside the inserting section 2. Inside the operating section 3, a pulley (not shown) coupled with the bending operation knob 36 is connected to a proximal end of each of the bending wires 37A and 37B. A distal end of each of the bending wires 37A and 37B is connected to a distal portion of the active bending section 22. By the bending operation with the bending operation knob 36, the bending wire 37A or the bending wire 37B is pulled, and the active bending section 22 bends. Additionally, the passive bending section 23 passively bends when an external force acts thereon.

Each of the bending wires 37A and 37B is inserted through a corresponding coil 38A or 38B. A proximal end of each of the coils 38A and 38B is extended up to an inside the operating section 3. Additionally, a distal end of ehac of the coils 38A and 38B is connected to an inner peripheral surface of the bending tube connecting portion 26. It is to be noted that in the present embodiment, the two bending wires 37A and 37B are disposed and the active bending section 22 is bendable in two directions, but, e.g., four bending wires may be provided and the active bending section 22 may be bendable in four directions.

Figure 4:
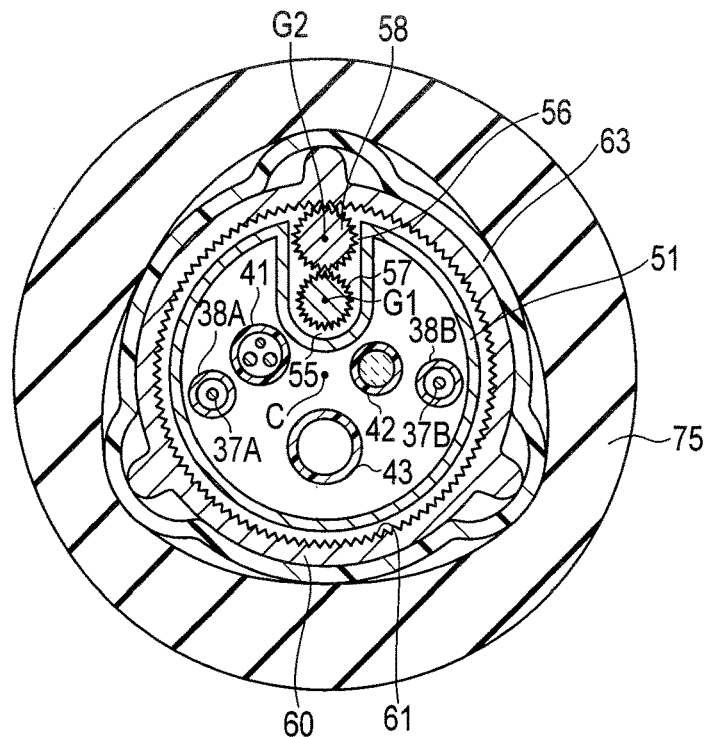
FIG. 4 is a cross-sectional view taken along the IV-IV line of FIG. 3.
Figure 5:
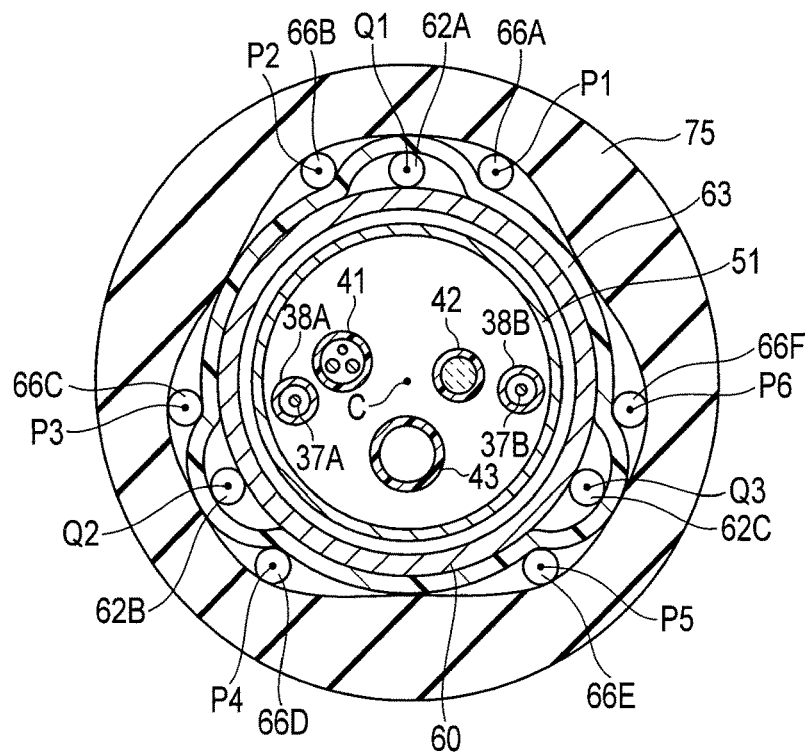
FIG. 5 is a cross-sectional view taken along the V-V line of FIG. 3.

As shown in FIG. 3 to FIG. 5, inside the inserting section 2, an imaging cable 41, a light guide 42 and a treatment tool channel tube 43 are extended along the longitudinal axis C. In the distal rigid section 21 (a distal portion of the inserting section 2), an imaging element (not shown) configured to image a subject is disposed. The imaging element performs the imaging of the subject through an observation window 46. One end of the imaging cable 41 is connected to the imaging element. The imaging cable 41 is extended through the inside of the inserting section 2, the inside of the operating section 3 and the inside of the universal cord 5, and its other end is connected to the image processing section 11 of the peripheral unit 10. The image processing section 11 performs image processing of the captured subject image, and generates the image of the subject. Further, the generated image of the subject is displayed in the display section 16.

Additionally, the light guide 42 is extended through the inside of the inserting section 2, the inside of the operating section 3 and the inside of the universal cord 5 and connected to the light source section 12 of the peripheral unit 10. Light emitted from the light source section 12 is guided by the light guide 42, to irradiate the subject from an illumination window 47 of the distal portion of the inserting section 2 (the distal rigid section 21).

As shown in FIG. 1, on the outer surface of the operating section 3, a treatment tool inserting portion 48 is disposed into which treatment tool such as forceps is to be inserted. The treatment tool channel tube 43 passes through the inside of the inserting section 2 and the inside of the operating section 3, and its one end is connected to the treatment tool inserting portion 48. The treatment tool inserted from the treatment tool inserting portion 48 passes through an inside of the treatment tool channel tube 43 to project from an opening 49 of the distal rigid section 21 toward the distal direction. Further, in a state where the treatment tool is projected from the opening 49 of the distal rigid section 21, a treatment by the treatment tool is performed.

As shown in FIG. 3, a base member 51 is provided in the relay connecting portion 27. A proximal portion of the passive bending section 23 is coupled with a distal portion of the base member 51 via a relay member 52. In consequence, the passive bending section 23 is coupled with the relay connecting portion 27. In addition, a distal portion of the flexible tube section 25 is connected to a proximal portion of the base member 51 via a relay member 53. In consequence, the flexible tube section 25 is coupled with the relay connecting portion 27.

As shown in FIG. 3 to FIG. 5, in the relay connecting portion 27, a hollow portion 55 is formed by the base member 51. The hollow portion 55 is opened toward an outer peripheral direction in an opening 56. Additionally, a driving gear 57 and a relay gear 58 are attached to the base member 51. The driving gear 57 is disposed in the hollow portion 55, and the relay gear 58 is disposed in the vicinity of the opening 56 of the hollow portion 55. The driving gear 57 meshes with the relay gear 58. The driving gear 57 is rotatable around a gear axis G1, and the relay gear 58 is rotatable around a gear axis G2.

A rotary cylindrical member 60 is attached to the base member 51 of the relay connecting portion 27. In a state where the inserting section 2 is inserted through the rotary cylindrical member 60, the rotary cylindrical member 60 is attached to the base member 51. The rotary cylindrical member 60 is rotatable relative to the inserting section 2 (the base member 51) in the periaxial direction of the longitudinal axis. On an inner peripheral surface of the rotary cylindrical member 60, an inner peripheral gear portion 61 is provided along the whole circumference in the direction around the longitudinal axis. The inner peripheral gear portion 61 meshes with the relay gear 58.

Three inner rollers 62A to 62C are attached to the rotary cylindrical member 60 in the present embodiment. The inner rollers 62A to 62C are arranged at substantially equal intervals in the periaxial direction of the longitudinal axis. Each of the inner rollers 62A to 62C has a corresponding roller axis (one of Q1 to Q3). Each of the inner rollers 62A to 62C is rotatable relative to the rotary cylindrical member 60 around the corresponding roller axis (one of Q1 to Q3). Additionally, the inner rollers 62A to 62C are rotatable integrally with the rotary cylindrical member 60 relative to the inserting section 2 (the base member 51) in the direction around the longitudinal axis.

Outer peripheral direction side part with respect to the rotary cylindrical member 60 and the inner rollers 62A to 62C is covered with a cylindrical cover member 63. A distal end of the cover member 63 is fixed to the base member 51 via an engaging member 65A, and a proximal end of the cover member 63 is fixed to the base member 51 via an engaging member 65B. At a fixing position of the distal end of the cover member 63 and a fixing position of the proximal end of the cover member 63, a space between the base member 51 and the cover member 63 is maintained liquid-tight. Consequently, there is prevented inflow of a liquid into the hollow portion 55, the rotary cylindrical member 60 and the inner rollers 62A to 62C positioned on an inner peripheral direction side of the cover member 63. Additionally, in a region where the inner rollers 62A to 62C are positioned in the periaxial direction of the longitudinal axis, the cover member 63 projects toward the outer peripheral direction. It is to be noted that the cover member 63 is fixed to the inserting section 2, and the rotary cylindrical member 60 and the inner rollers 62A to 62C are rotatable relative to the cover member 63 in the periaxial direction of the longitudinal axis.

As shown in FIG. 5, six outer rollers 66A to 66F are attached to an inner peripheral surface of the proximal side taper portion 35. The outer rollers 66A to 66F are positioned on an outer peripheral direction side with respect to the cover member 63. As to the periaxial direction of the longitudinal axis, the inner roller 62A is positioned between the outer roller 66A and the outer roller 66B, and the inner roller 62B is positioned between the outer roller 66C and the outer roller 66D. Additionally, as to the direction around the longitudinal axis, the inner roller 62C is positioned between the outer roller 66E and the outer roller 66F. Each of the outer rollers 66A to 66F has a corresponding roller axis (one of P1 to P6). Each of the outer rollers 66A to 66F is rotatable relative to the cover member 63 and the proximal side taper portion 35 around the corresponding roller axis (one of P1 to P6). Additionally, the outer rollers 66A to 66F are rotatable integrally with the spiral unit 30 relative to the inserting section 2 (the base member 51) in the periaxial direction of the longitudinal axis.

When the rotary cylindrical member 60 rotates in one side of the periaxial direction of the longitudinal axis, the inner roller 62A presses the outer roller 66A or the outer roller 66B. Similarly, the inner roller 62B presses the outer roller 66C or the outer roller 66D, and the inner roller 62C presses the outer roller 66E or the outer roller 66F. In consequence, the driving force is transmitted to the spiral unit 30 from the inner rollers 62A to 62C, and the spiral unit 30 rotates relative to the inserting section 2 and the cover member 63 toward one side of the periaxial direction of the longitudinal axis (as to the direction around the longitudinal axis).

It is to be noted that each of the inner rollers 62A to 62C rotates around the corresponding roller axis (one of Q1 to Q3), and hence a friction between each of the inner rollers 62A to 62C and the cover member 63 decreases. Similarly, each of the outer rollers 66A to 66F rotates around the roller axis (one of P1 to P6), and hence a friction between each of the outer rollers 66A to 66F and the cover member 63 decreases. In consequence, the driving force is appropriately transmitted to the spiral unit 30 from the inner rollers 62A to 62C, and the spiral unit 30 appropriately rotates.

As shown in FIG. 1 and FIG. 2, the operating section 3 is coupled with a motor housing 71. In the motor housing 71, a motor 72 that is a driving member is housed. One end of a motor cable 73 is connected to the motor 72. The motor cable 73 is extended through the inside of the operating section 3 and the inside of the universal cord 5, and its other end is connected to the drive control section 13 of the peripheral unit 10. When an electric power is supplied from the drive control section 13 via the motor cable 73, the motor 72 is driven, and a motor shaft 75 rotates around a motor axis M. When the motor 72 is driven, the driving force to drive (rotate) the spiral unit 30 that is the motion section is generated.

A relay gear 76 is attached to the motor shaft 75. Additionally, inside the operating section 3, there is disposed a driving gear 77 that meshes with the relay gear 76. The relay gear 76 is rotatable integrally with the motor shaft 75 around the motor axis M. When the motor 72 is driven, the driving force generated in the motor 72 is transmitted to the driving gear 77 via the relay gear 76. In consequence, the driving gear 77 rotates around a gear axis G3.

As shown in FIG. 2 and FIG. 3, a shaft 81 is extended along a shaft axis S inside the flexible tube section 25 of the inserting section 2. The shaft 81 has a flexibility and is extended from a first extending direction toward a second extending direction. It is to be noted that in the present embodiment, the first extending direction is the proximal direction, and the second extending direction is the distal direction. A proximal end of the shaft 81 (an end on a first extending direction side) is connected to the driving gear 77. When the driving force to rotate the spiral unit 30 is generated in the motor 72, the driving force is transmitted to the shaft 81 via the relay gear 76 and the driving gear 77 from the proximal direction (the first extending direction). In consequence, a rotational torque □ acts on the shaft 81, and the shaft 81 rotates around the shaft axis S. When the shaft 81 rotates, the driving force to actuate the spiral unit 30 is transmitted from the proximal direction (the first extending direction) to the distal direction (the second extending direction).

A distal end of the shaft 81 (the end on a second extending direction side) is connected to the driving gear 57. The driving force to rotate the spiral unit 30 is transmitted from the shaft 81 to the driving gear 57 toward the distal direction (the second extending direction). When the driving force is transmitted, the driving gear 57 rotates around the gear axis G1. When the driving gear 57 rotates, the relay gear 58 rotates around the gear axis G2, and the driving force is transmitted to the rotary cylindrical member 60 via the relay gear 58. When the driving force is transmitted to the rotary cylindrical member 60, the rotary cylindrical member 60 rotates in one side of the periaxial direction of the longitudinal axis (as to the direction around the longitudinal axis), and the driving force is transmitted to the spiral unit 30 as described above. In consequence, the spiral unit 30 as the motion section is driven.

As shown in FIG. 2 and FIG. 3, inside the flexible tube section 25, a flexible guide tube 82 is extended from the proximal direction (the first extending direction) toward the distal direction (the second extending direction). A distal end of the guide tube 82 is connected to the base member 51. The inside of the guide tube 82 communicates with the hollow portion 55. The shaft 81 is inserted through the guide tube 82. Therefore, the shaft 81 is extended through an inside of the guide tube 82, and an outer peripheral portion of the shaft 81 is covered with the guide tube 82.

As shown in FIG. 3, the flexible tube section 25 includes a helical tube (flex) 85 made of a metal, a reticular tube 86 made of a metal and disposed to cover an outer peripheral direction side of the flex 85, and a flexible tube shell 87 made of a resin and disposed to cover an outer peripheral direction side of the reticular tube 86. The helical tube 85 has a constitution in which a band made of the metal is spirally extended around the longitudinal axis C, and has a flexibility. Additionally, the reticular tube 86 has a constitution in which the metal is disposed in a mesh shape, and has a flexibility. Furthermore, the flexible tube shell 87 is made of a soft material and has a flexibility. Therefore, the flexible tube section 25 has the flexibility, and also bends due to the action of the external force. That is, the flexible tube section 25 is a shape-variable tube that can be deformed by the action of the external force. Additionally, an inner peripheral surface of the helical tube 85 forms a tube inner peripheral surface 89 that is the inner peripheral surface of the flexible tube section 25.

The flexible tube section 25 is extended along a tube axis T from the proximal direction (the first extending direction) to the distal direction (the second extending direction). In the present embodiment, the tube axis T matches the longitudinal axis C of the endoscope device 1 (the inserting section 2). When the flexible tube section 25 that is the shape-variable tube bends at a tube bending radius Rt that is a tube radius boundary value Rt0 or more, the flexible tube section elastically returns. That is, the bend of the flexible tube section 25 at the tube bending radius Rt of the tube radius boundary value Rt0 or more is an elastic deformation. On the other hand, when the flexible tube section 25 bends at the tube bending radius Rt smaller than the tube radius boundary value Rt0, the flexible tube section does not elastically return. That is, the bend of the flexible tube section 25 at the tube bending radius Rt smaller than the tube radius boundary value Rt0 is a plastic deformation.

FIG. 6 is a view showing a constitution of the shaft 81. As shown in FIG. 6, the shaft 81 is formed by disposing layers (two layers in the present embodiment) of cylindrical densely wound coils 90A and 90B. In each of the densely wound coils 90A and 90B, a corresponding linear member 91A or 91B is spirally extended around the shaft axis S. Here, one side of a periaxial directions of the shaft axis is defined as a first rotating direction (a direction of an arrow Y1 of FIG. 6), and a direction opposite to the first rotating direction is defined as a second rotating direction (a direction of an arrow Y2 of FIG. 6). As a position in the densely wound coil 90A is directed from the proximal direction (the direction of the arrow C1 of FIG. 6) toward the distal direction (the direction of the arrow C2 of FIG. 6), the linear member 91A is directed toward the first rotating direction. Additionally, as a position in the densely wound coil 90B is directed from the proximal direction (the first extending direction) toward the distal direction (the second extending direction), the linear member 91B is directed toward the second rotating direction.

In the shaft 81 of such a constitution as mentioned above, tightening states of the densely wound coils 90A and 90B vary between a first rotating state to rotate in the first rotating direction and a second rotating state to rotate in the second rotating direction. Consequently, between the first rotating state and the second rotating state, a rigidity of the shaft 81 changes. In the present embodiment, for example, the tightening state of the densely wound coil 90B that is the outermost layer has a large influence on the rigidity of the shaft 81. In the first rotating state, a tightening force by the densely wound coil 90B decreases, and the rigidity of the shaft 81 lowers. On the other hand, in the second rotating state, the tightening force by the densely wound coil 90B increases, and the rigidity of the shaft 81 heightens. Therefore, in the first rotating state, the rigidity of the shaft 81 is lower than in the second rotating state. The rigidity of the shaft 81 lowers, and hence in the first rotating state, transmitting properties of the driving force to rotate the spiral unit 30 are lower than in the second rotating state.

Additionally, the shaft 81 has a flexibility, and hence the shaft is deformed when the external force acts thereon. When the shaft 81 bends at a shaft bending radius Rs that is a shaft radius boundary value Rs0 or more, the shaft elastically returns. That is, the bend of the shaft 81 at the shaft bending radius Rs of the shaft radius boundary value Rs0 or more is the elastic deformation. On the other hand, when the shaft 81 bends at the shaft bending radius Rs smaller than the shaft radius boundary value Rs0, the shaft does not elastically return. That is, the bend of the shaft 81 at the shaft bending radius Rs smaller than the shaft radius boundary value Rs0 is the plastic deformation. The shaft 81 is plastically deformed, and hence the driving force to rotate the spiral unit 30 cannot be transmitted. That is, in the state where the shaft 81 is plastically deformed, the driving force is not transmitted from the proximal direction (the first extending direction) toward the distal direction (the second extending direction). FIG. 7 is a diagram showing a relation between the rotational torque □ that acts on the shaft 81 and the shaft radius boundary value Rs0 of the shaft bending radius Rs. As shown in FIG. 7, the shaft radius boundary value Rs0 is not determined as one value, but changes in accordance with an amount of the rotational torque □ to rotate the shaft 81. As the rotational torque □ increases, a burden to be loaded onto the shaft 81 increases, and hence the shaft 81 is easy to be plastically deformed. In consequence, the larger the rotational torque □ is, the larger the shaft radius boundary value Rs0 of the shaft bending radius Rs becomes.

Next, a function and an effect of the endoscope device 1 that is an inserting device of the present embodiment will be described. When the endoscope apparatus 1 is used, the inserting section 2 is inserted into the lumen in a state where the spiral unit 30 is attached to the inserting section 2. Further, in a state where the fin portion 32 abuts on the lumen walls, the motor 72 is driven, the driving force is transmitted to the shaft 81 as described above, and the shaft 81 rotates around the shaft axis S. Consequently, in the shaft 81, the driving force is transmitted from the proximal direction (the first extending direction) toward the distal direction (the second extending direction). Further, as described above, the driving force is transmitted from the shaft 81 to the spiral unit 30, and the spiral unit 30 rotates relative to the inserting section 2 in one side of the periaxial direction of the longitudinal axis (as to the direction around the longitudinal axis). In a state where a pressing force is received from the lumen paries in the inner peripheral direction by the fin portion 32, the spiral unit 30 is rotated in one side of the periaxial direction of the longitudinal axis, and hence the impulsive force in the distal direction or the proximal direction acts on the inserting section 2.

FIG. 8 is a view showing a state where the inserting section 2 to which the spiral unit 30 is attached is inserted from an anal 201 into a large intestine 202. As shown in FIG. 8, when the endoscope device 1 is used in observation of the large intestine 202, the inserting section 2 is inserted until the spiral unit 30 positioned on the outer peripheral direction side of the passive bending section 23 is positioned in a deep region of the large intestine 202. In this case, the flexible tube section 25 is bent by the external force from the lumen walls in a splenic flexure 203, a hepatic flexure 205 and an appendix 206 of the large intestine 202. The bend of the flexible tube section 25 in the splenic flexure 203, the hepatic flexure 205 and the appendix 206 is a deformation in a range of the elastic deformation, and the flexible tube section 25 bends at the tube bending radius Rt of the tube radius boundary value Rt0 or more. Therefore, the flexible tube section 25 that is the shape-variable tube is elastically returnable even when the flexible tube section bends in the splenic flexure 203, the hepatic flexure 205 and the appendix 206.

Figure 9:
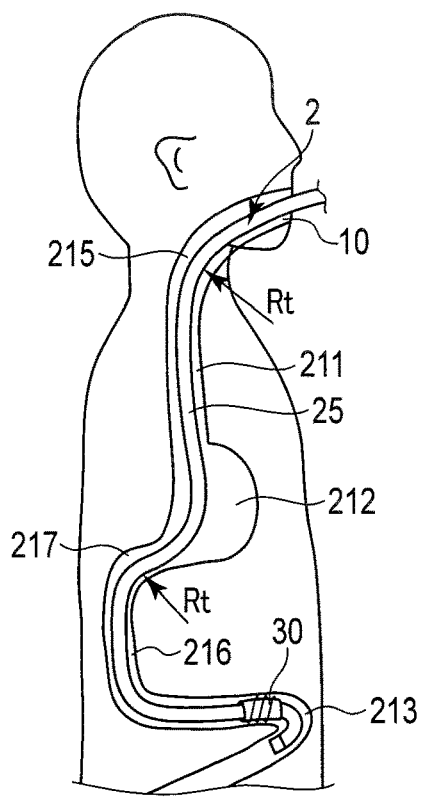
FIG. 9 is a schematic view showing a state where the inserting section to which the spiral unit according to the first embodiment is attached is inserted from a mouth through an esophagus and a stomach into a small intestine.

FIG. 9 is a view showing a state where the inserting section 2 to which the spiral unit 30 is attached is inserted from a mouth 210 through an esophagus 211 and a stomach 212 into a small intestine 213. As shown in FIG. 9, the endoscope device 1 might be used in a use application other than the observation of the large intestine 202 shown in FIG. 8. In this case, the inserting section 2 is inserted until the spiral unit 30 positioned on the outer peripheral direction side of the passive bending section 23 is positioned in the small intestine 213. In this case, the flexible tube section 25 is bent by the external force from the lumen paries in a pharynx 215 between the mouth 210 and the esophagus 211 and a pylorus 217 between the stomach 212 and a duodenum 216. The bend of the flexible tube section 25 in the pharynx 215 and the pylorus 217 is a deformation in a range of the elastic deformation, and the flexible tube section 25 bends at the tube bending radius Rt of the tube radius boundary value Rt0 or more. Therefore, the flexible tube section 25 that is the shape-variable tube is elastically returnable even in a case where the flexible tube section bends in the pharynx 215 and the pylorus 217.

Figure 10:
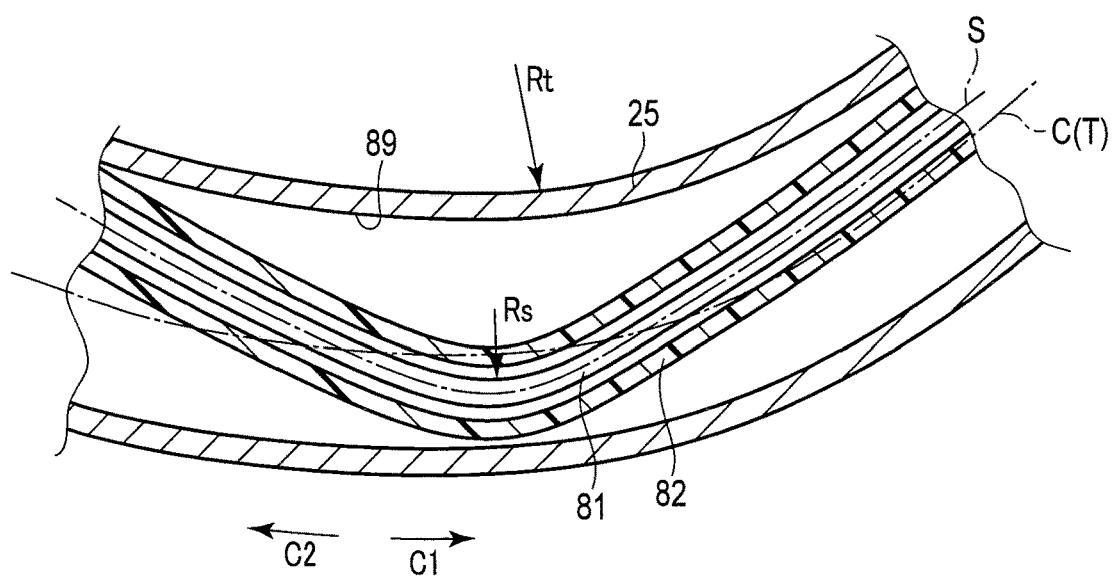
FIG. 10 is a cross-sectional view schematically showing an inner constitution of a flexible tube section in a state where the flexible tube section according to the first embodiment is bent in an elastically returnable range.

As described above, in use of the endoscope device 1 that is the inserting device, the flexible tube section 25 that is the shape-variable tube might bend in the elastically returnable range. FIG. 10 is a view showing an inner constitution of the flexible tube section 25 in the state where the flexible tube section 25 bends in the elastically returnable range. It is to be noted that FIG. 10 only shows the flexible tube section 25, the shaft 81 and the guide tube 82, and omits the imaging cable 41, the light guide 42 and the like. Additionally, in FIG. 10, the flexible tube section 25 bends in the elastically returnable range, and hence the tube bending radius Rt of the flexible tube section 25 is the tube radius boundary value Rt0 or more.

As shown in FIG. 10, the flexible tube section 25 bends, and hence the external force acts on the shaft 81 and the guide tube 82 extended inside the flexible tube section 25, thereby bending the shaft 81 and the guide tube 82. In this case, the shaft 81 is deformed in the elastically returnable range, and is not deformed in a state where the elastic return is impossible, but the shaft rotates around the shaft axis S.

Therefore, the shaft bending radius Rs of the shaft 81 is the shaft radius boundary value Rs0 or more. That is, in the state where the flexible tube section 25 that is the shape-variable tube bends in the elastically returnable range, the shaft 81 rotates without being deformed in the elastically non-returnable state. The shaft 81 is not plastically deformed, and hence in the state where the flexible tube section 25 bends in the elastically returnable range, the driving force to drive the spiral unit 30 is appropriately transmitted from the proximal direction (the first extending direction) toward the distal direction (the second extending direction). Therefore, even in the state where the flexible tube section 25 bends in the elastically returnable range, the driving force can appropriately be transmitted to the spiral unit 30 that is the motion section via the shaft 81.

Additionally, as described above, the shaft 81 has a lower rigidity in the first rotating state to rotate in the first rotating direction than in the second rotating state to rotate in the second rotating direction. Consequently, in the first rotating state, the shaft 81 is easier to be deformed and the transmitting properties of the driving force are lower than in the second rotating state. In the present embodiment, even in the case where the shaft 81 rotates toward the first rotating state in which the rigidity lowers, the shaft 81 rotates in the first rotating direction without being deformed in the elastically non-returnable state, in the state where the flexible tube section 25 bends in the elastically returnable range. Therefore, even in the case where the flexible tube section 25 bends in the elastically returnable range in the first rotating state of the shaft 81, the driving force to actuate the spiral unit 30 can appropriately be transmitted from the proximal direction (the first extending direction) toward the distal direction (the second extending direction) in the shaft 81. It is to be noted that in such a constitution, in the second rotating state in which the transmitting properties of the driving force heighten, needless to say, the driving force can appropriately be transmitted from the proximal direction (the first extending direction) toward the distal direction (the second extending direction) in the shaft 81, even in the case where the flexible tube section 25 bends in the elastically returnable range.

In addition, the shaft radius boundary value Rs0 changes in accordance with the amount of the rotational torque □ to rotate the shaft 81. In the present embodiment, irrespective of the amount of the rotational torque □ that acts on the shaft 81, the shaft 81 rotates without being deformed in the elastically non-returnable state, in the state where the flexible tube section 25 bends in the elastically returnable range. Consequently, even when the rotational torque □ that acts on the shaft 81 has any amount, the driving force to drive the spiral unit 30 can appropriately be transmitted via the shaft 81 from the proximal direction (the first extending direction) toward the distal direction (the second extending direction), in the state where the flexible tube section 25 bends in the elastically returnable range.

Figure 11:
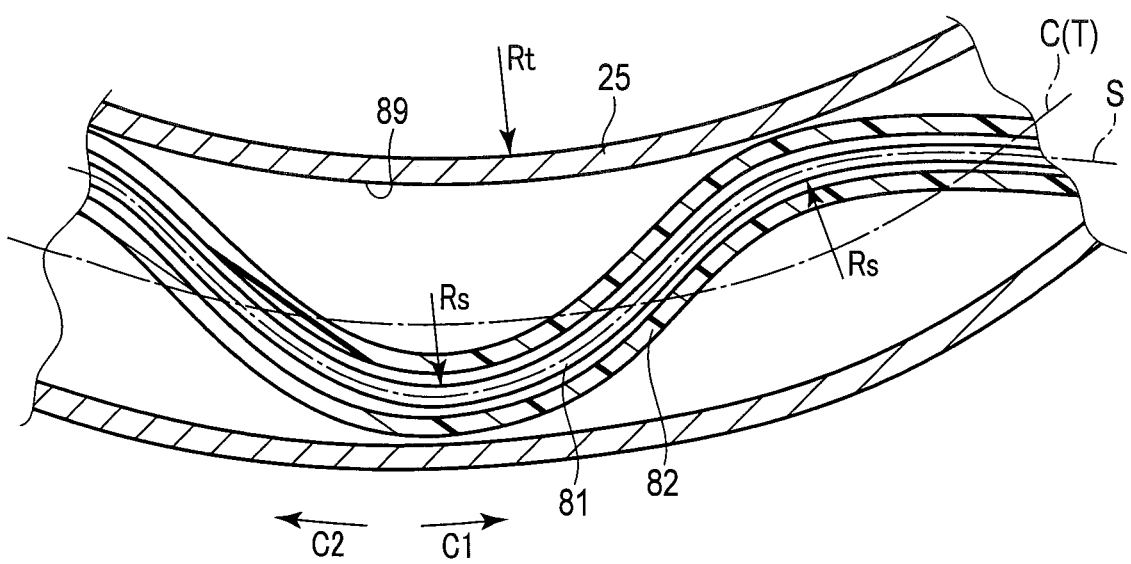
FIG. 11 is a schematic view showing a state where the shaft extended inside the flexible tube section according to the first embodiment is twisted.

FIG. 11 is a view showing a state where the shaft 81 extended inside the flexible tube section 25 is twisted. It is to be noted that FIG. 11 only shows the flexible tube section 25, the shaft 81 and the guide tube 82, and omits the imaging cable 41, the light guide 42 and the like. As shown in FIG. 11, in the use of the endoscope device 1, the shaft 81 might be twisted by the abovementioned bend of the flexible tube section 25 in the elastically returnable range. In this case, in a portion where the shaft 81 is twisted, the shaft 81 is spirally extended around the tube axis T (the longitudinal axis C) from the proximal direction (the first extending direction) toward the distal direction (the second extending direction). In a portion where the shaft 81 is spirally extended, the shaft 81 is bent and the shaft 81 is deformed.

Here, in the present embodiment, in the state where the shaft bending radius Rs of the shaft 81 is the shaft radius boundary value Rs0 or more, the guide tube 82 abuts on the tube inner peripheral surface 89 of the flexible tube section 25. That is, while the shaft 81 is deformed in the elastically returnable range, the guide tube 82 abuts on the tube inner peripheral surface 89 of the flexible tube section 25. The guide tube 82 abuts on the tube inner peripheral surface 89, and hence the pressing force acts on the shaft 81 extended inside the guide tube 82, from the tube inner peripheral surface 89 toward the tube axis T. The pressing force acts on the shaft 81, thereby maintaining the shaft bending radius Rs of the shaft 81 at a size of the shaft radius boundary value Rs0 or more. Consequently, even in the state where the shaft 81 is twisted, the shaft 81 is deformed in the elastically returnable range, and is not plastically deformed. Consequently, even in the state where the shaft 81 is twisted, the driving force to move the spiral unit 30 is appropriately transmitted from the proximal direction (the first extending direction) toward the distal direction (the second extending direction) in the shaft 81. Therefore, even in the state where the shaft 81 is twisted, the driving force can appropriately be transmitted to the spiral unit 30 that is the motion section via the shaft 81.

Second Embodiment

Figure 12:
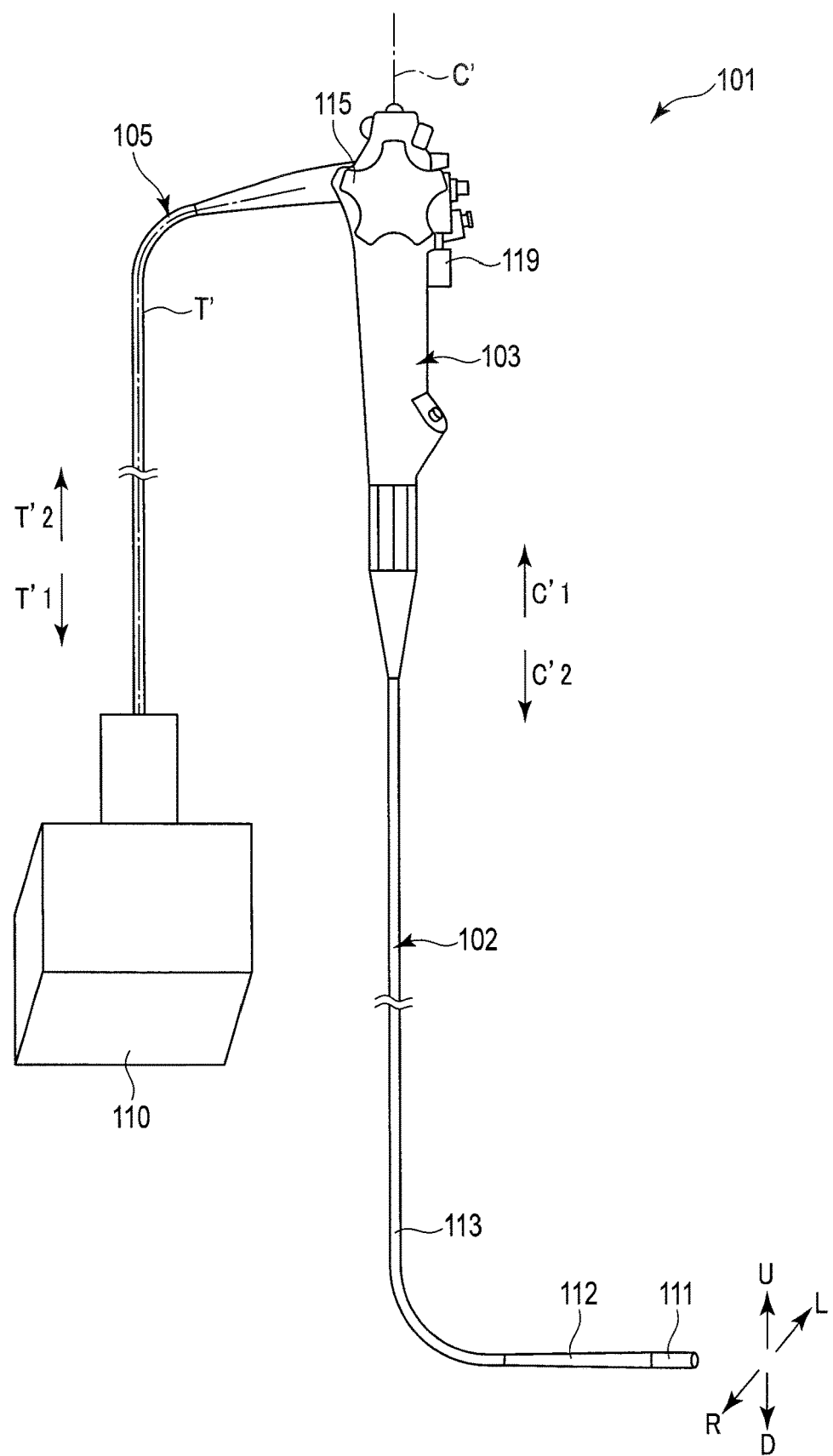
FIG. 12 is a perspective view schematically showing an endoscope device according to a second embodiment of the present invention.

In the first embodiment, the shaft 81 extended in the flexible tube section 25 is rotated, thereby transmitting the driving force to drive the spiral unit 30 that is the motion section. A second embodiment that is another use application example of the present invention will be described with reference to FIG. 12 to FIG. 16. FIG. 12 is a view showing an endoscope device 101 that is an inserting device of the present embodiment.

As shown in FIG. 12, the endoscope device 101 has a longitudinal axis C'. Further, one side of direction parallel to the longitudinal axis C' is a proximal direction (a direction of an arrow C'1 of FIG. 12), and a direction opposite to the proximal direction is a distal direction (a direction of an arrow C'2 of FIG. 12). The endoscope device 101 includes an inserting section (an endoscope inserting section) 102 extended along the longitudinal axis C', and an operating section (an endoscope operating section) 103 provided on a proximal direction side with respect to the inserting section 102. The inserting section 102 is extended along the longitudinal axis C', and inserted into a body cavity when the endoscope apparatus 101 is used.

The operating section 103 is connected to one end of a universal cord 105. The universal cord 105 is extended along a tube axis T' from a first extending direction toward a second extending direction. The other end of the universal cord 105 is connected to a peripheral unit 110. Here, one side of direction parallel to the tube axis T' is the first extending direction (a direction of an arrow T'1 of FIG. 12), and a direction opposite to the first extending direction is the second extending direction (a direction of an arrow T'2 of FIG. 12). In the universal cord 105, the first extending direction is a direction toward the peripheral unit 110, and the second extending direction is a direction toward the operating section 103.

The inserting section 102 includes a distal rigid section 111 that forms a distal end of the inserting section 102, a bending section 112 disposed on the proximal direction side with respect to the distal rigid section 111, and a flexible tube section 113 provided on the proximal direction side with respect to the bending section 112. The bending section 112 performs a bending motion when a driving force is transmitted thereto. That is, the bending section 112 is a motion section that is provided in the inserting section 102 and is driven when the driving force is transmitted thereto. The bending section 112 is bendable in bending UD directions (a direction of an arrow U and a direction of an arrow D of FIG. 12) and bending LR directions (a direction of an arrow L and a direction of an arrow R of FIG. 12).

It is to be noted that in the present embodiment, similarly to the first embodiment, an imaging cable (41), a light guide (42) and the like are provided, and in the peripheral unit 110, an image processing section (11), a light source section (12) and the like are disposed. These components are similar to those of the first embodiment, and hence detailed descriptions are omitted. In the following description, a constitution to drive the bending section 112 will specifically be described.

FIG. 13 is a view showing a constitution to transmit the driving force to the bending section 112. As shown in FIG. 12 and FIG. 13, a bending operation knob 115 is disposed in the operating section 103. The bending operation knob 115 is turned, thereby generating the driving force to bend the bending section 112 in one of the bending UD directions. Inside the operating section 103, a UD pulley 116A is disposed. A proximal end of each of UD bending wires 117U and 117D is connected to the UD pulley 116A. The bending operation knob 115 is turned, thereby turning the UD pulley 116A. When the UD pulley 116A is turned, the UD bending wires 117U and 117D move along the longitudinal axis C', and the UD bending wire 117U or the UD bending wire 117D is pulled toward the proximal direction. A distal end of each of the UD bending wires 117U and 117D are connected to a distal portion of the bending section 112. The UD bending wire 117U or the UD bending wire 117D is pulled, thereby transmitting the driving force generated in the bending operation knob 115 to the bending section 112 via the UD pulley 116A and the UD bending wires 117U and 117D. In consequence, the bending section 112 performs the bending motion, and bends in one side of the bending UD directions (as to the bending UD direction).

Additionally, in the operating section 103, a bending operation dial 119 is disposed. By the bending operation dial 119, a bending operation to bend the bending section 112 in one side of the bending LR directions is input. Inside the operating section 103, a detecting section 121 configured to detect the input of the bending operation with the bending operation dial 119 is provided. The detecting section 121 is connected to one end of an electric signal line 122. The electric signal line 122 passes through an inside of the universal cord 105, and its other end is connected to a drive control section 123 of the peripheral unit 110. The drive control section 123 is, for example, a control device including a CPU and an ASIC.

In an end portion on a first extending direction side in the universal cord 105, a motor 125 that is a driving member is provided. The motor 125 is electrically connected to the drive control section 123 via an electric wire 126. The drive control section 123 supplies an electric power to the motor 125 on the basis of the detection result in the detecting section 121. When the electric power is supplied, the motor 125 is driven, and a motor shaft 127 rotates around a motor axis M'. The motor 125 is driven, thereby generating a driving force to drive the bending section 112 that is a motion section (to bend the bending section in one side of the bending LR directions).

A relay gear 128 is attached to the motor shaft 127. Additionally, inside the universal cord 105, a driving gear 129 that meshes with the relay gear 128 is disposed. The relay gear 128 is rotatable integrally with the motor shaft 127 around the motor axis M'. When the motor 125 is driven, the driving force generated in the motor 125 is transmitted to the driving gear 129 via the relay gear 128. In consequence, the driving gear 129 rotates around a gear shaft G4.

In the universal cord 105, a shaft 131 is extended along a shaft axis S'. The shaft 131 has a flexibility and is extended from the first extending direction (the direction of the arrow T'1 of FIG. 13) toward the second extending direction (the direction of the arrow T'2 of FIG. 13). One end of the shaft 131 (an end on a first extending direction side) is connected to the driving gear 129. The driving force to bend the bending section 112 is generated in the motor 125, thereby transmitting the driving force to the shaft 131 via the relay gear 128 and the driving gear 129 from the first extending direction. In consequence, a rotational torque $\square$' acts on the shaft 131, and the shaft 131 rotates around the shaft axis S'. The shaft 131 rotates, thereby transmitting the driving force to actuate the bending section 112 from the first extending direction to the second extending direction.

Additionally, in the universal cord 105, a flexible guide tube 132 is extended from the first extending direction to the second extending direction. The shaft 131 is inserted through the guide tube 132. Therefore, the shaft 131 is extended through an inside of the guide tube 132, and an outer peripheral portion of the shaft 131 is covered with the guide tube 132.

Inside the operating section 103, a bevel gear 133 is disposed. The other end of the shaft 131 (an end on a second extending direction side) is connected to the bevel gear 133. The driving force to bend the bending section 112 is transmitted from the shaft 131 to the bevel gear 133 toward the second extending direction. The bevel gear 133 includes a relay gear (a first gear) 135 that rotates around a gear axis G5 when the driving force is transmitted via the shaft 131.

Additionally, inside the operating section 103, a spur gear (a second gear) 136 that meshes with the relay gear 135 is disposed. The number of teeth of the spur gear 136 is larger than the number of teeth of the relay gear 135. Consequently, the driving force is transmitted from the relay gear 135, and hence the spur gear 136 rotates around a gear shaft G6 at a rotational angular velocity smaller than that of the relay gear 135. In consequence, the driving force to bend the bending section 112 is amplified between the relay gear (the first gear) 135 and the spur gear (the second gear) 136. Therefore, the relay gear 135 and the spur gear 136 form an amplifying unit 137 configured to amplify the driving force transmitted from the shaft 131 toward the second extending direction.

Inside the operating section 103, an LR pulley 116B is disposed. A proximal end of each of LR bending wires 117L and 117R is connected to the LR pulley. The spur gear 136 rotates, thereby transmitting the driving force generated in the motor 125 to the LR pulley 116B, to turn the LR pulley 116B. When the LR pulley 116B is turned, the LR bending wires 117L and 117R move along the longitudinal axis C', and the LR bending wire 117L or the LR bending wire 117R is pulled toward the proximal direction. A distal end of each of the LR bending wires 117L and 117R is connected to a distal portion of the bending section 112. The LR bending wire 117L or the LR bending wire 117R is pulled, and hence the driving force transmitted from the motor 125 to the spur gear 136 is transmitted to the bending section 112 via the LR pulley 116B and the LR bending wires 117L and 117R. Consequently, the bending section 112 performs the bending motion, and bends in one side of the bending-LR directions (as to the bending LR direction). That is, when the driving force generated in the motor 125 is transmitted to the bending section 112, the bending section as the motion section is driven.

FIG. 14 is a view showing a constitution of the universal cord 105. As shown in FIG. 14, the universal cord 105 includes a helical tube (flex) 141 made of a metal, a reticular tube 142 made of a metal and disposed to cover an outer peripheral direction side of the flex 141, and a cord shell 143 made of a resin and disposed to cover an outer peripheral direction side of the reticular tube 142. The helical tube 141 has a constitution in which a band made of the metal is spirally extended around the tube axis T', and has a flexibility, similarly to the helical tube 85 of the first embodiment. Additionally, the reticular tube 142 has a constitution in which the metal is disposed in a mesh shape, and has a flexibility, similarly to the reticular tube 86 of the first embodiment. Furthermore, the cord shell 143 is made of a soft material and has a flexibility similarly to the flexible tube shell 87 of the first embodiment. Therefore, the universal cord 105 has the flexibility and bends by an action of an external force. That is, the universal cord 105 is a shape-variable tube that can be deformed by the action of the external force. Additionally, an inner peripheral surface of the helical tube 141 forms a tube inner peripheral surface 145 that is an inner peripheral surface of the universal cord 105.

When the universal cord 105 that is the shape-variable tube bends at a tube bending radius R't of a tube radius boundary value R't0 or more, the universal cord elastically returns, similarly to the flexible tube section 25 of the first embodiment. That is, the bend of the universal cord 105 at the tube bending radius R't of the tube radius boundary value R't0 or more is an elastic deformation. On the other hand, a bend of the universal cord 105 at the tube bending radius R't smaller than the tube radius boundary value R't0 is a plastic deformation.

Additionally, the shaft 131 is formed similarly to the shaft 81 of the first embodiment. Consequently, in the shaft 131, similarly to the shaft 81 of the first embodiment, a rigidity of the shaft 131 changes between a first rotating state to rotate toward a first rotating direction and a second rotating state to rotate toward a second rotating direction. That is, in the first rotating state, the rigidity of the shaft 131 is lower than in the second rotating state. The rigidity of the shaft 131 is low, and hence in the first rotating state, transmitting properties of the driving force to bend the bending section 112 are lower than in the second rotating state.

Additionally, the shaft 131 has a flexibility and is therefore deformed when the external force acts thereon. When the shaft 131 bends at a shaft bending radius R's of a shaft radius boundary value R's0 or more, the shaft elastically returns similarly to the shaft 81 of the first embodiment. That is, the bend of the shaft 131 at the shaft bending radius R's of the shaft radius boundary value R's0 or more is the elastic deformation. On the other hand, a bend of the shaft 131 at the shaft bending radius R's smaller than the shaft radius boundary value R's0 is the plastic deformation. When the shaft 131 is plastically deformed, the driving force to bend the bending section 112 cannot be transmitted. That is, in a state where the shaft 131 is plastically deformed, the driving force is not transmitted from the first extending direction toward the second extending direction. Additionally, in the shaft 131, similarly to the shaft 81 of the first embodiment, the shaft radius boundary value R's0 is not determined as one value, and changes in accordance with an amount of the rotational torque D' to rotate the shaft 131.

Next, a function and an effect of the endoscope device 101 that is the inserting device of the present embodiment will be described. When the endoscope device 101 is used, the inserting section 102 is inserted into a lumen. When the bending section 112 is bent in one of the bending UD directions, the bending operation knob 115 is turned, thereby generating the driving force to bend the bending section 112. The generated driving force is transmitted to the bending section 112 via the UD pulley 116A and the UD bending wires 117U and 117D. Consequently, the bending section 112 bends in one side of the bending UD directions (as to the bending UD direction).

Additionally, in a case where the bending section 112 is bent in one of the bending LR directions, the bending operation is input by the bending operation dial 119. Consequently, the detecting section 121 detects the input of the bending operation, and the drive control section 123 supplies the electric power to the motor 125. In consequence, the motor 125 is driven, the driving force is transmitted to the shaft 131 as described above, and the shaft 131 rotates around the shaft axis S'. Consequently, in the shaft 131, the driving force is transmitted from the first extending direction toward the second extending direction. Further, as described above, the driving force is transmitted from the shaft 81 to the bending section 112 via the LR pulley 116B and the LR bending wires 117L and 117R. In consequence, the bending section 112 bends in one side of the bending LR directions (as to the bending LR direction).

FIG. 15 is a view showing an extended state of the universal cord 105 from the peripheral unit 110 when the endoscope device 101 is used. As shown in FIG. 15, when the endoscope apparatus 101 is used, the universal cord 105 that is the shape-variable tube might hang down between the peripheral unit 110 and the operating section 103 due to gravity that is the external force. In this case, the universal cord 105 bends in a portion where the universal cord hangs down. The bend of the universal cord 105 in the portion where the universal cord hands down is a deformation in a range of an elastic deformation, and the universal cord 105 bends at the tube bending radius R't of the tube radius boundary value R't0 or more. Therefore, the universal cord 105 that is the shape-variable tube is elastically returnable even in a case where the cord bends in the portion where the cord hangs down.

FIG. 16 is a view showing an extended state of the universal cord 105 from the operating section 103 in a certain use state of the endoscope device 101. As shown in FIG. 16, when the endoscope device 101 is used, an operator might turn the inserting section 102 and the operating section 103 around the longitudinal axis C'. When the operating section 103 is turned, the external force acts on the universal cord 105 whose end on the second extending direction side is connected to the operating section 103, and thereby the universal cord 105 bends in its second-extending-direction-side end portion. The bend of the universal cord 105 in the end portion on the second extending direction side is the deformation in the range of the elastic deformation, and the universal cord 105 bends at the tube bending radius R't of the tube radius boundary value R't0 or more. Therefore, the universal cord 105 that is the shape-variable tube is elastically returnable also in a case where the universal cord bends in the vicinity of the operating section 103.

As described above, in the use of the endoscope device 1 that is the inserting device, the universal cord 105 that is the shape-variable tube might bend in an elastically returnable range. In this case, the universal cord 105 bends in the elastically returnable range, and hence the tube bending radius R't of the universal cord 105 is the tube radius boundary value R't0 or more.

Here, in the present embodiment, similarly to the first embodiment; in the state where the universal cord 105 that is the shape-variable tube bends in the elastically returnable range, the shaft 131 is deformed in the elastically returnable range, and rotates around the shaft axis S' without being deformed in a state where the elastic return is impossible. Therefore, the shaft bending radius R's of the shaft 131 is the shaft radius boundary value R's0 or more. The shaft 131 is not plastically deformed, and hence in the state where the universal cord 105 bends in the elastically returnable range, the driving force to drive the bending section 112 is appropriately transmitted from the first extending direction toward the second extending direction in the shaft 131. Therefore, also in the state where the universal cord 105 bends in the elastically returnable range, the driving force can appropriately be transmitted to the bending section 112 that is the motion section via the shaft 131.

Additionally, also in the present embodiment, similarly to the first embodiment, also in a case where the shaft 131 rotates in the first rotating state in which the rigidity lowers, the shaft 131 rotates toward the first rotating direction without being deformed in the state where the elastic return is impossible, in the state where the universal cord 105 bends in the elastically returnable range. Therefore, also in the case where the universal cord 105 bends in the elastically returnable range in the first rotating state of the shaft 131, the driving force to move the bending section 112 can appropriately be transmitted from the first extending direction toward the second extending direction via the shaft 131.

Additionally, in the present embodiment, similarly to the first embodiment, irrespective of the amount of the rotational torque □' that acts on the shaft 131, the shaft 131 rotates without being deformed in the state where the elastic return is impossible, in the state where the universal cord 105 bends in the elastically returnable range. Consequently, even when the rotational torque □' that acts on the shaft 131 has any amount, the driving force to drive the bending section 112 can appropriately be transmitted from the first extending direction toward the second extending direction in the shaft 131, in the state where the universal cord 105 bends in the elastically returnable range.

Additionally, in the present embodiment, there is disposed the amplifying unit 137 configured to amplify the driving force transmitted by the shaft 131. The amplifying unit 137 is disposed in a portion closer to the bending section 112 that is the motion section than the shaft 131, so that it is possible to decrease the rotational torque □' that acts on the shaft 131. In consequence, burdens in a case where the shaft 131 rotates can be decreased.

In addition, the tube inner peripheral surface 145 of the universal cord 105 exerts a pressing force on the shaft 131 toward the tube axis T' in a state where the shaft 131 is twisted, similarly to the tube inner peripheral surface 89 of the first embodiment. The pressing force acts on the shaft 131, thereby maintaining the shaft bending radius R's of the shaft 131 at a size of the shaft radius boundary value R's0 or more. Consequently, even in the state where the shaft 131 is twisted, the shaft 131 is deformed in the elastically returnable range, and is not plastically deformed. In consequence, also in the state where the shaft 131 is twisted, the driving force to actuate the bending section 112 is appropriately transmitted from the first extending direction toward the second extending direction in the shaft 131. Therefore, also in the state where the shaft 131 is twisted, the driving force can appropriately be transmitted to the bending section 112 that is the motion section via the shaft 131. It is to be noted that in the present embodiment, only in a case where the bending section 112 is bent and driven in the bending LR direction utilizing the driving force generated by the motor 125 that is an electric motor is shown, but it is not limited to this example. That is, an electric motor (not shown) constituted similarly to the electric motor 125 may be used to generate the driving force also in the case where the bending section 112 is bent and driven in the bending UD direction. In this case, by a constitution similar to the constitution to transmit the driving force to bend the bending section 112 in the bending LR direction in the second embodiment, the driving force to bend and driven the bending section 112 in the bending UD direction is transmitted to the bending section 112.

(Modification)

Figure 17:
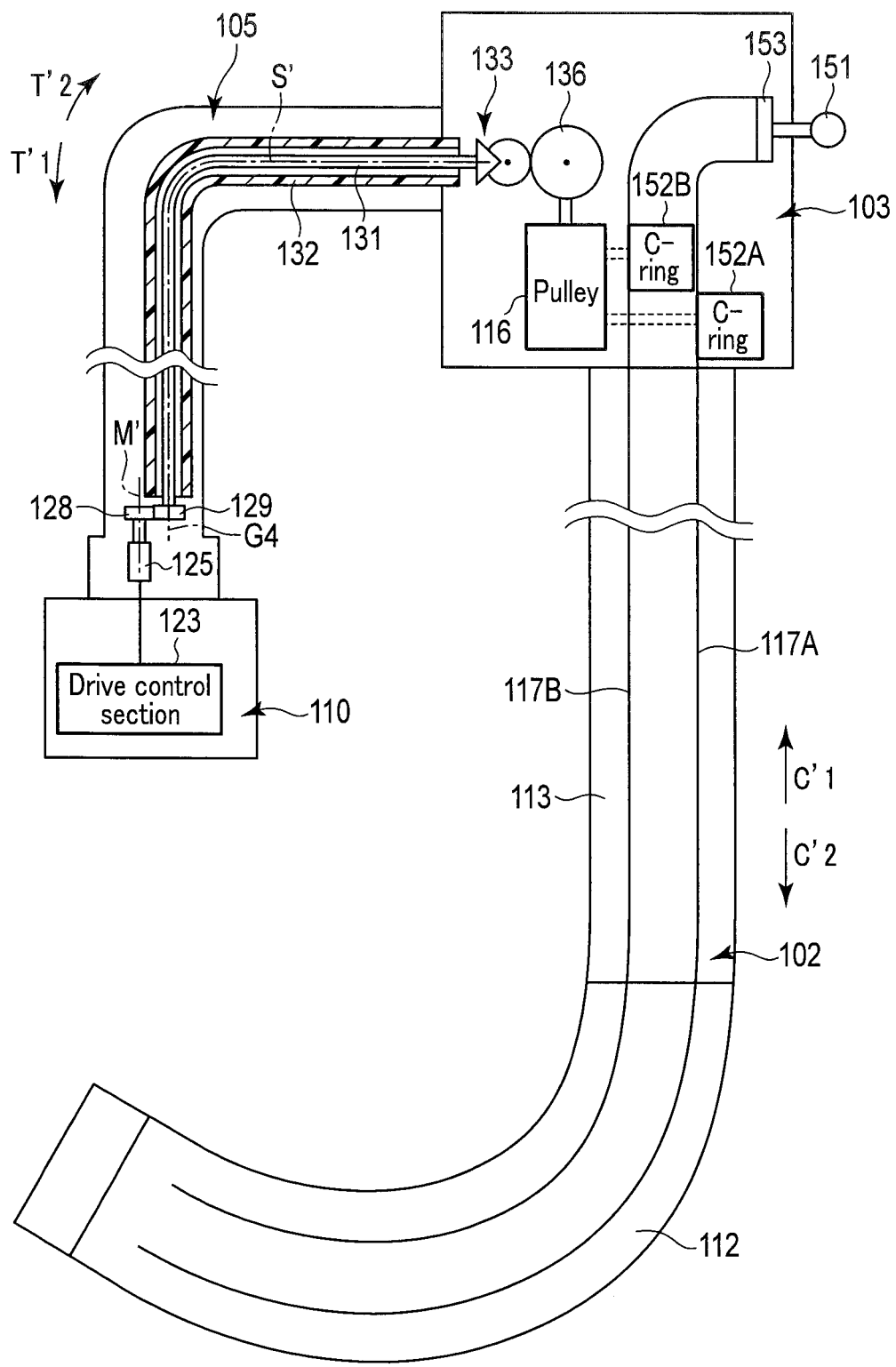
FIG. 17 is a schematic view showing a constitution to transmit a driving force to a bending section according to a first modification of the present invention.
Figure 18:
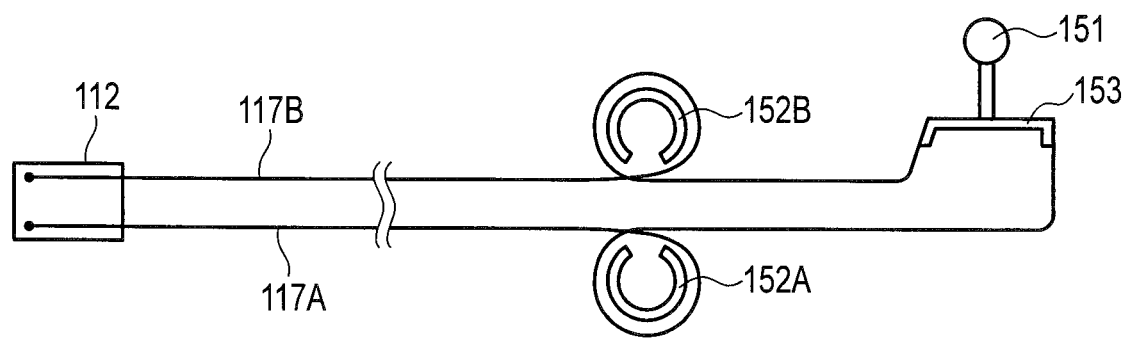
FIG. 18 is a schematic view showing an extended state of each of bending wires according to the first modification.
Figure 19:
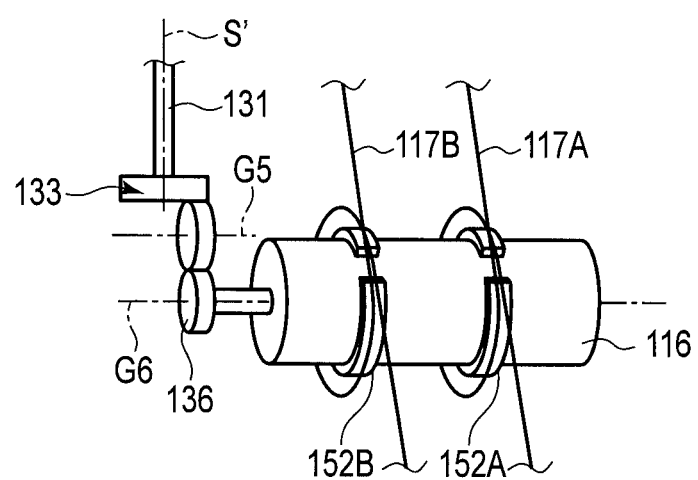
FIG. 19 is a schematic view showing constitutions of a pulley and C-rings according to the first modification.

With reference to FIG. 17 to FIG. 19, a first modification is described below as a use application example in which a bending section 112 is a motion section and a shaft 131 is extended in a universal cord 105 that is a shape-variable tube, similarly to the second embodiment. It is to be noted that in the first modification, the same parts as in the second embodiment are denoted with the same reference signs, and the descriptions are omitted.

FIG. 17 is a view showing a constitution to transmit a driving force to the bending section 112 in an endoscope device 101 of the present modification. In the present modification, when the driving force is transmitted to the bending section 112, the bending section 112 performs a bending motion toward a first bending direction that is one of directions perpendicular to a longitudinal axis C, or a second bending direction opposite to the first bending direction. As shown in FIG. 17, in the present modification, a bending operation joystick 151 is disposed in place of a bending operation dial 119. The bending operation joystick 151 is tilted, thereby inputting the bending operation to bend the bending section 112 in the first bending direction or the second bending direction.

Also in the present modification, similarly to the second embodiment, a motor 125 is driven, thereby generating a driving force to bend the bending section 112. The driving force generated in the motor 125 is transmitted to the shaft 131 via a relay gear 128 and a driving gear 129, and in the shaft 131, the driving force is transmitted from a first extending direction toward a second extending direction. Further, the driving force is transmitted to a pulley 116 via a bevel gear 133 and a spur gear 136.

However, in the present modification, differently from the second embodiment, the motor 125 is always driven when the endoscope device 101 is used. Therefore, the driving force is always transmitted from the motor 125 to the pulley 116. In consequence, the pulley 116 always rotates.

FIG. 18 is a view showing an extended state of bending wires 117A and 117B. As shown in FIG. 17 and FIG. 18, a distal end of each of the bending wires 117A and 117B is connected to a distal portion of the bending section 112. Additionally, in the present modification, a proximal end of each of the bending wires 117A and 117B is not connected to the pulley 116. In the present modification, C-rings 152A and 152B are disposed inside the operating section 103. Each of the bending wires 117A and 117B is wound around an outer peripheral surface of the corresponding C-ring 152A or 152B. Further, the proximal end of the each bending wire 117A or 117B wound around the corresponding C-ring 152A or 152B is connected to a plate portion 153. By the input of the bending operation, the plate portion 153 tilts integrally with the bending operation joystick 151. The plate portion 153 tilts, thereby pulling the bending wire 117A or the bending wire 117B toward a proximal direction.

FIG. 19 is a view showing a constitution of the pulley 116 and the C-rings 152A and 152B. As shown in FIG. 19, the C-rings 152A and 152B are provided to cover an outer peripheral portion of the pulley 116. In a state where each of the bending wires 117A and 117B is not pulled, the C-rings 152A and 152B do not come in contact with the pulley 116. Consequently, the driving force transmitted from the motor 125 to the pulley 116 is not transmitted to the bending wires 117A and 117B.

When the bending wire 117A is pulled, a diameter of the C-ring 152A decreases, and the C-ring 152A abuts on the outer peripheral portion of the pulley 116. Consequently, the pulling of the bending wire 117A is assisted by the driving force transmitted to the pulley 116. Additionally, when the bending wire 117B is pulled, a diameter of the C-ring 152B is decreased, and the C-ring 152B abuts on the outer peripheral portion of the pulley 116. Consequently, the pulling of the bending wire 117B is assisted by the driving force transmitted to the pulley 116. As described above, when the bending wire 117A or the bending wire 117B is pulled, the bending motion of the bending section 112 in the first bending direction or the second bending direction is assisted by the driving force transmitted to the pulley 116. The present modification also has a function and an effect similar to those of the second embodiment. It is to be noted that in a certain example, the first bending direction and the second bending direction match bending UD directions, and in another example, the first bending direction and the second bending direction match bending LR directions. Additionally, when two C-rings of constitutions similar to the C-rings 152A and 152B are added and two bending wires of constitutions similar to the bending wires 117A and 117B are added, the constitution of the present modification is also applicable to a case where the bending section 112 is bendable in four directions that are the bending UD directions and the bending LR directions.

Additionally, in the abovementioned embodiments and modification, the guide tube (82; 132) that covers the outer peripheral portion of the shaft (81; 131) is provided, but the guide tube (82; 132) does not have to be provided. Additionally, the motion section is not limited to the spiral unit 30 and the bending section 112. Similarly, the shape-variable tube is not limited to the flexible tube section 25 and the universal cord 105.

Additionally, in the abovementioned embodiments and modification, as the example of the inserting device, the endoscope device (1; 101) has been described, but the inserting device is not limited to the endoscope device (1; 101). For example, the abovementioned constitution may be applied to an inserting section of a manipulator device that is the inserting device.

That is, in the abovementioned embodiments and the like, the motion section (30; 112) is provided in the inserting section (2; 102) or attached to the inserting section (2; 102), and driven by transmitting the driving force thereto. Further, the shape-variable tube (25; 105) has the tube axis (T; T') extended from the first extending direction (C1; T'1) toward the second extending direction (C2; T'2), and has the flexibility. Further, the shape-variable tube (25; 105) elastically returns in the case where the tube bends at the tube bending radius (Rt; R't) of the tube radius boundary value (Rt0; R't0) or more. Additionally, the shaft (81; 131) has the shaft axis (S; S') extended inside the shape-variable tube (25; 105) from the first extending direction (C1; T'1) toward the second extending direction (C2; T'2), and rotates around the shaft axis (S; S') by the action of the rotational torque ($\square$; $\square$'), thereby transmitting the driving force to drive the motion section (30; 112) from the first extending direction (C1; T'1) toward the second extending direction (C2; T'2). Further, the shaft (81; 131) elastically returns in the case where the shaft bends at the shaft bending radius (Rs; R's) of the shaft radius boundary value (Rs0; R's0) or more, and rotates without being deformed in the state where the elastic return is impossible, in the state where the shape-variable tube (25; 105) bends in the elastically returnable range.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An inserting device comprising:
an inserting section which is extended along a longitudinal axis from a proximal side toward a distal side;
a rotor which is attached to the inserting section, and which is configured to rotate around the longitudinal axis when a driving force is transmitted thereto;
a shape-variable tube which forms a part of the inserting section, and which has a flexibility, the shape-variable tube being extended along the longitudinal axis with the longitudinal axis serving as a central axis, the shape-variable tube being elastically returnable to a tube straight extended shape, in which the shape-variable tube is extended straight, in a case where the shape-variable tube bends at a tube bending radius of a tube radius boundary value or greater from the tube straight extended shape;
at least one of an imaging cable and a light guide which has a member axis as a central axis and is disposed inside the shape-variable tube from the proximal side toward the distal side along the member axis;
a shaft which has a shaft axis as a central axis, and which is disposed inside the shape-variable tube from the proximal side toward the distal side along the shaft axis,
the shaft being disposed outside the at least one imaging cable and the light guide in an inner space of the shape-variable tube,
the shaft being configured to rotate around the shaft axis by an action of a rotational torque so that the shaft transmits the driving force to rotate the rotor from the proximal side toward the distal side,
a sectional area of the inner space of the shape-variable tube perpendicular to the longitudinal axis being larger than a sum of a sectional area of the at least one of the imaging cable and the light guide perpendicular to the member axis and a sectional area of the shaft perpendicular to the shaft axis,
the shaft being elastically returnable to a shaft straight extended shape, in which the shaft is extended straight, in a case where the shaft bends at a shaft bending radius of a shaft radius boundary value or greater,
the shaft being bendable at the shaft bending radius smaller than the tube bending radius in the inner space of the shape-variable tube when the tube bends at the tube bending radius of the tube radius boundary value or greater, the shaft bending radius being constantly maintained at the shaft radius boundary value or greater in the inner space of the shape-variable tube when the shaft rotates and the tube bending radius is constantly maintained at the tube radius boundary value or greater, wherein the shape-variable tube includes a tube inner peripheral surface which is configured to exert a pressing force on the shaft toward the longitudinal axis so that the tube inner peripheral surface maintains the shaft bending radius at the shaft radius boundary value or greater in the inner space of the shape-variable tube; and a cylindrical spiral unit which includes a fin portion spirally extended from the proximal side toward the distal side, and which is attached to an outer peripheral side of the inserting section, the spiral unit being configured to rotate in a periaxial direction of the longitudinal axis when the driving force is transmitted thereto by the rotation of the rotor, the spiral unit being configured to rotate in a state where the fin portion is pressed toward an inner peripheral side so as to exert an impulsive force onto the inserting section in the distal side or the proximal side.

2. The inserting device according to claim 1,
wherein the shaft radius boundary value of the shaft bending radius of the shaft changes in accordance with an amount of the rotational torque to rotate the shaft, and wherein the shaft bending radius is constantly maintained at the shaft radius boundary value or greater in the inner space of the shape-variable tube when the shaft rotates and the tube bending radius is constantly maintained at the tube radius boundary value or greater, irrespective of the amount of the rotational torque.

3. The inserting device according to claim 1,
wherein in the shaft, a rigidity is lower and transmitting properties of the driving force are lower in a first rotating state to rotate toward a first rotating direction that is one side of a periaxial direction of the shaft axis than in a second rotating state to rotate toward a second rotating direction that is a direction opposite to the first rotating direction, and wherein the shaft bending radius is constantly maintained at the shaft radius boundary value or greater in the inner space of the shape-variable tube when the shaft rotates toward the first rotating direction in the first rotating state and the tube bending radius is constantly maintained at the tube radius boundary value or greater.

4. The inserting device according to claim 1, further comprising:
a driving source which is configured to generate the driving force to rotate the rotor, and configured to transmit the generated driving force to the shaft from the proximal side so as to exert the rotational torque onto the shaft.

5. The inserting device according to claim 1, further comprising:
an amplifying unit configured to amplify the driving force transmitted from the shaft toward the distal side.

6. The inserting device according to claim 5,
wherein the amplifying unit includes a first gear which is configured to rotate when the driving force is transmitted thereto via the shaft, and a second gear which meshes with the first gear and which is configured to rotate at a rotational angular velocity smaller than that of the first gear when the driving force is transmitted from the first gear thereto.

7. The inserting device according to claim 1, further comprising:
a guide tube which is disposed outside the at least one of the imaging cable and the light guide in the inner space of the shape-variable tube from the proximal side toward the distal side along the shaft, and through which the shaft is inserted, the guide tube covering an outer peripheral portion of the shaft.

* * * * *